(12) United States Patent
Bansal et al.

(10) Patent No.: US 9,233,955 B2
(45) Date of Patent: Jan. 12, 2016

(54) PROCESS FOR THE PREPARATION OF AZILSARTAN MEDOXOMIL

(75) Inventors: Deepak Bansal, Uttar Pradesh (IN); Himanchal Mishra, Uttar Pradesh (IN); Shailendr Kumar Dubey, Uttar Pradesh (IN); Alka Srivastava Choudhary, Uttar Pradesh (IN); Dharam Vir, Uttar Pradesh (IN); Ashutosh Agarwal, Uttar Pradesh (IN)

(73) Assignee: Jubilant Life Sciences, Ltd., Uttar Pradesh (IN)

( * ) Notice: Subject to any disclaimer, the term of this patent is extended or adjusted under 35 U.S.C. 154(b) by 61 days.

(21) Appl. No.: 13/983,521

(22) PCT Filed: Jan. 24, 2012

(86) PCT No.: PCT/IB2012/000090
§ 371 (c)(1),
(2), (4) Date: Aug. 2, 2013

(87) PCT Pub. No.: WO2012/107814
PCT Pub. Date: Aug. 16, 2012

(65) Prior Publication Data
US 2013/0317230 A1  Nov. 28, 2013

(30) Foreign Application Priority Data
Feb. 8, 2011  (IN) .............................. 315/DEL/2011

(51) Int. Cl.
*C07D 413/10* (2006.01)
*C07D 413/14* (2006.01)

(52) U.S. Cl.
CPC ............ *C07D 413/10* (2013.01); *C07D 413/14* (2013.01)

(58) Field of Classification Search
CPC ........................... C07D 413/10; C07D 413/14
See application file for complete search history.

(56) References Cited

U.S. PATENT DOCUMENTS 5,243,054 A  9/1993 Naka et al.
7,157,584 B2  1/2007 Kuroita et al.

OTHER PUBLICATIONS

Alpegiania, Marco, et al., "On the Preparation of 4-Hydroxymethyl-5-Methyl-1,3-Dioxol-2-One", Synthetic Communications, Taylor & Francis Group, Philadephia, PA, vol. 22, No. 9, Jan. 1, 1992, pp. 1277-1282, XP008150982, ISSN: 0039-7911, 001: 10.1080100397919208019309 [retrieved on Sep. 24, 2006].
Kohara, Yasuhisa, et al. "Synthesis and angiotensin II receptor antagonistic activities of benzimidazole derivatives bearing acidic heterocycles as novel tetrazole bioisosteres", Journal of Medicinal Chemistry, American Chemical Society, US; vol. 39, No. 26, Dec. 20, 1996, pp. 5228-5235, XP002448276, ISSN: 0022-2623,001.
The International Bureau of WIPO, International Preliminary Report on Patentability for International Patent Application No. PCT/IB2012/000090, Aug. 22, 2013; 11 pages.

*Primary Examiner* — Samantha Shterengarts
(74) *Attorney, Agent, or Firm* — Fish & Tsang, LLP

(57) ABSTRACT

The present invention relates to an improved process for the preparation of azilsartan or its esters or salts thereof. Specifically, the invention provides a method for the preparation of highly pure methyl 1-[[2'-(4,5-dihydro-5-oxo-4H-1,2,4-oxadiazol-3-yl)biphenyl-4-yl]methyl]-2-ethoxy-1H-benzimidazole-7-carboxylate an intermediate compound of formula (4) for azilsartan medoxomil with reduced content of desethyl impurity. The invention also involves the use of highly pure methyl 1-[[2'-(4,5-dihydro-5-oxo-4H-1,2,4-oxadiazol-3-yl)biphenyl-4-yl]methyl]-2-ethoxy-1H-benzimidazole-7-carboxylate in the preparation of azilsartan or its esters or salts thereof, preferably medoxomil with reduced content of desethyl impurity.

12 Claims, No Drawings

PROCESS FOR THE PREPARATION OF AZILSARTAN MEDOXOMIL

FIELD OF INVENTION

The present invention provides an improved process for the preparation of azilsartan or its esters or salts thereof, with less number of steps, high yield, high degree of purity with less impurities and economically viable on commercial scale. Specifically, the invention provides a method for the preparation of highly pure methyl 1-[[2'-(4,5-dihydro-5-oxo-4H-1,2,4-oxadiazol-3-yl)biphenyl-4-yl]methyl]-2-ethoxy-1H-benzimidazole-7-carboxylate an intermediate compound of formula (4) for azilsartan medoxomil with reduced content of desethyl impurity. Furthermore, the invention involves the use of highly pure methyl 1-[[2'-(4,5-dihydro-5-oxo-4H-1,2,4-oxadiazol-3-yl)biphenyl-4-yl]methyl]-2-ethoxy-1H-benzimidazole-7-carboxylate in the preparation of azilsartan or its esters or salts thereof, preferably azilsartan medoxomil with reduced content of desethyl impurity.

BACKGROUND OF THE INVENTION

Azilsartan medoxomil i.e. (5-methyl-2-oxo-1,3-dioxol-4-yl)methyl 2-ethoxy-1-([2'-(5-oxo-4,5-dihydro-1,2,4-oxadiazol-3-yl)biphenyl-4-yl]methyl)-1H-benzimidazole-7-carboxylate (1) and salts thereof has the uses such as a strong and long lasting angiotensin II antagonistic activity and hypotensive action, and an insulin sensitizing activity, and which is useful as an agent for the prophylaxis or treatment of circulatory diseases such as hypertension, cardiac diseases (cardiac hypertrophy, cardiac failure, cardiac infarction and the like), nephritis, stroke and the like and metabolic diseases such as diabetes and the like (U.S. Pat. No. 7,157,584). Azilsartan medoxomil is the prodrug of 2-ethoxy-1-([2'-(5-oxo-4,5-dihydro-1,2,4-oxadiazol-3-yl)biphenyl-4-yl]methyl)-1H-benzimidazole-7-carboxylic acid.

(1)

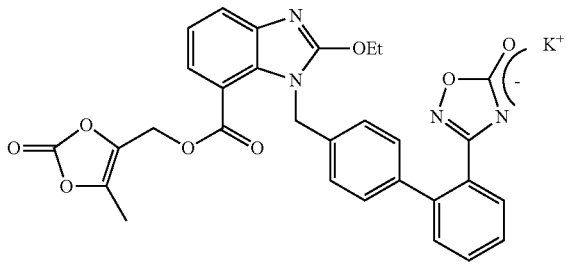

(1A)

Methods of preparing benzimidazole derivative useful as an angiotensin II receptor antagonist such as azilsartan medoxomil and salt thereof such as monopotassium salt (IA) are described in U.S. Pat. No. 5,243,054 (herein after referred as U.S. '054 patent).

The U.S. '054 patent describes several synthetic routes for preparing azilsartan. According to one synthetic process, azilsartan is prepared by the synthetic route as depicted below in Scheme 1. According to Scheme 1 cyanobiphenyl derivative compound of formula (2) reacts with hydroxylamine hydrochloride in a conventional organic solvent to give hydroxyamidino derivative of formula (3), which on further cyclization in presence of a base and chloroformic acid ester yielded the 1,2,4-oxadiazol derivative compound of formula (4). 1,2,4-oxadiazol derivative compound of formula (4) was further hydrolyzed in presence of a base to obtain azilsartan (5). Also, J. Med. Chem. Vol. 39, No. 26, 5230-5237 (1996) follows the same reaction sequence with minor changes in reagents such as use of triethylamine as base during the conversion of cyano group to hydroxyamidino derivative of formula (3); use of 2-ethylhexylchloroformate instead of ethylchloroformate as cyclizing agent with compound of formula (3).

Scheme 1

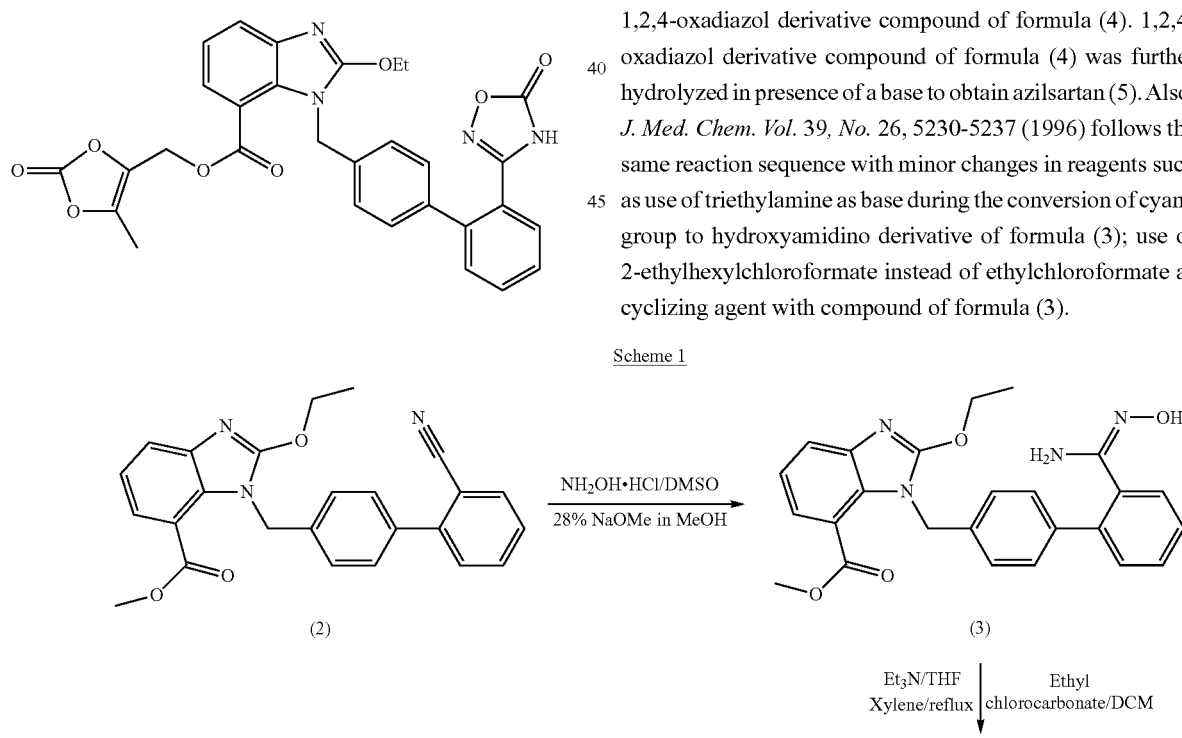

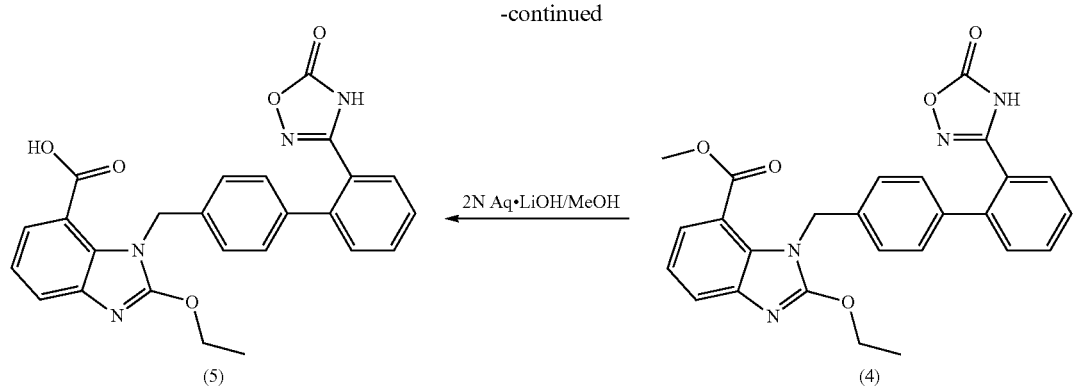

According to another method disclosed in U.S. '054 for the preparation of azilsartan (Scheme 2), ethoxycarboimidoyl biphenyl benzimidazole derivative of compound of formula (6) reacts with ethylchloroformate in presence of 2,6-dimethylpyridine as base gives N-methoxycarbonyl ethoxycarboimidoylbiphenyl benzimidazole derivative of compound of formula (7). The resulting N-methoxycarbonyl ethoxycarboimidoyl biphenyl benzimidazole compound of formula (7) can be converted to 1,2,4-oxadiazol derivative compound of formula (4) by either of the two ways: (i) by treating the compound of formula (7) with hydroxylamine hydrochloride in presence of sodium methoxide; (ii) by reacting compound of formula (7) with methyl chloroformate in presence of 2,4,6-trimethylpyridine to obtain a residue, which on further addition to a mixture of hydroxylamine hydrochloride and sodium methoxide under reflux yielded compound of formula (4). 1,2,4-Oxadiazol derivative compound of formula (4) thus obtained is further hydrolyzed in presence of a base to obtain azilsartan (5).

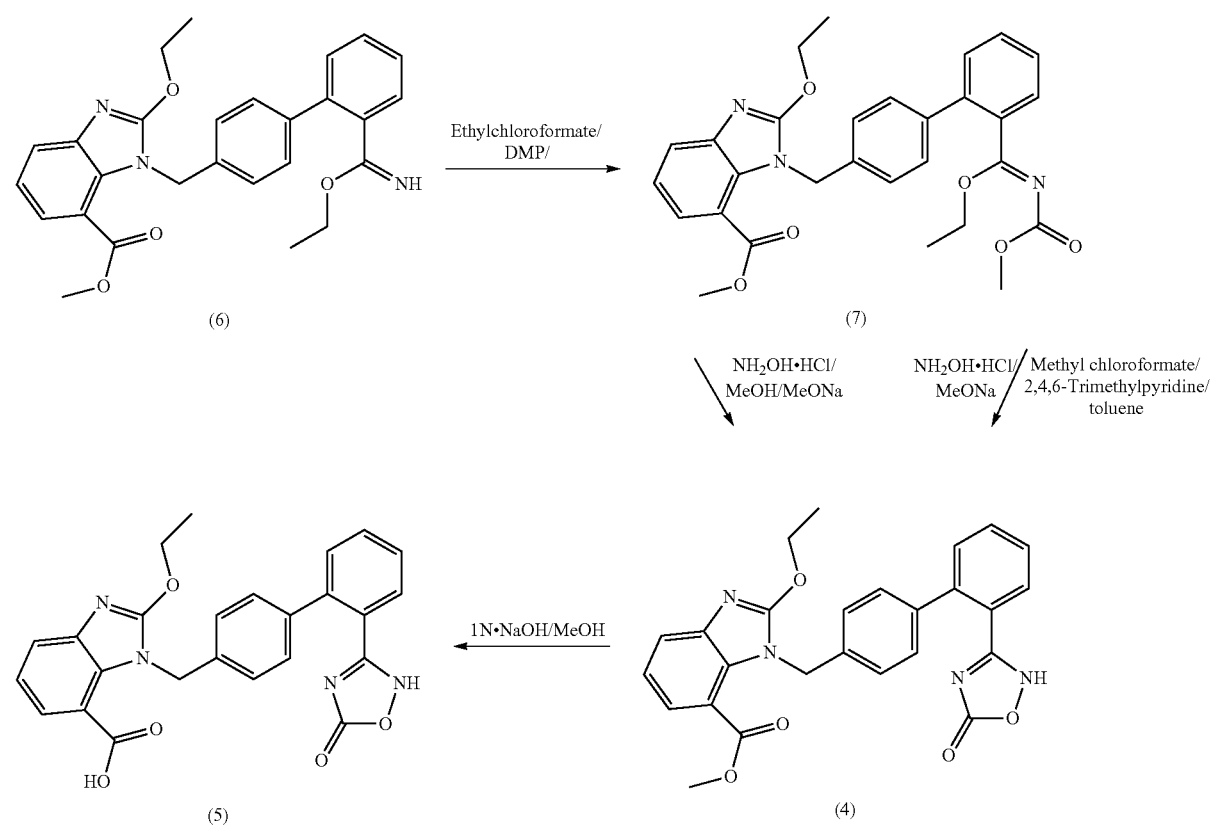

According to one another method for the preparation of azilsartan disclosed in U.S. '054 (Scheme 3), cyanobiphenyl aminobenzoate derivative compound of formula (8) reacts with hydroxylamine hydrochloride in presence of triethylamine subsequently followed by addition of ethyl chlorocarbonate to give ethoxycarbonyloxycarbamimidoyl derivative of formula (9). The resulting ethoxycarbonyloxycarbamimidoyl derivative of formula (9) can be converted to 1,2,4-oxadiazol derivative compound of formula (4) by either of the two ways: (i) by treating the compound of formula (9) with potassium carbonate; (ii) by reacting compound of formula (9) with 1,8-diazabicyclo[5.4.0]undec-7-ene (DBU). 1,2,4-Oxadiazol derivative compound of formula (4) thus obtained is further hydrolyzed in presence of a base to obtain azilsartan (5).

rities in azilsartan medoxomil or any active pharmaceutical ingredient (API) are undesirable and might be harmful, as they would be carried over to pharmaceutical compositions, used for human consumption.

According to U.S. '054 patent (Scheme 1), the preparation of 1,2,4-oxadiazol derivative compound of formula (4) by reacting cyano biphenyl derivative compound of formula (2) with hydroxylamine hydrochloride, as depicted in Scheme 1, yields about 10-12% of the desethyl impurity of formula (10), which accounts for the yield loss and impair the quality of the product.

According to U.S. '054 patent (Scheme 1), cyanobiphenyl derivative compound of formula (2) reacts with hydroxylamine hydrochloride in presence of sodium methoxide as base to give hydroxyamidino derivative of formula (3). Also, Scheme 3

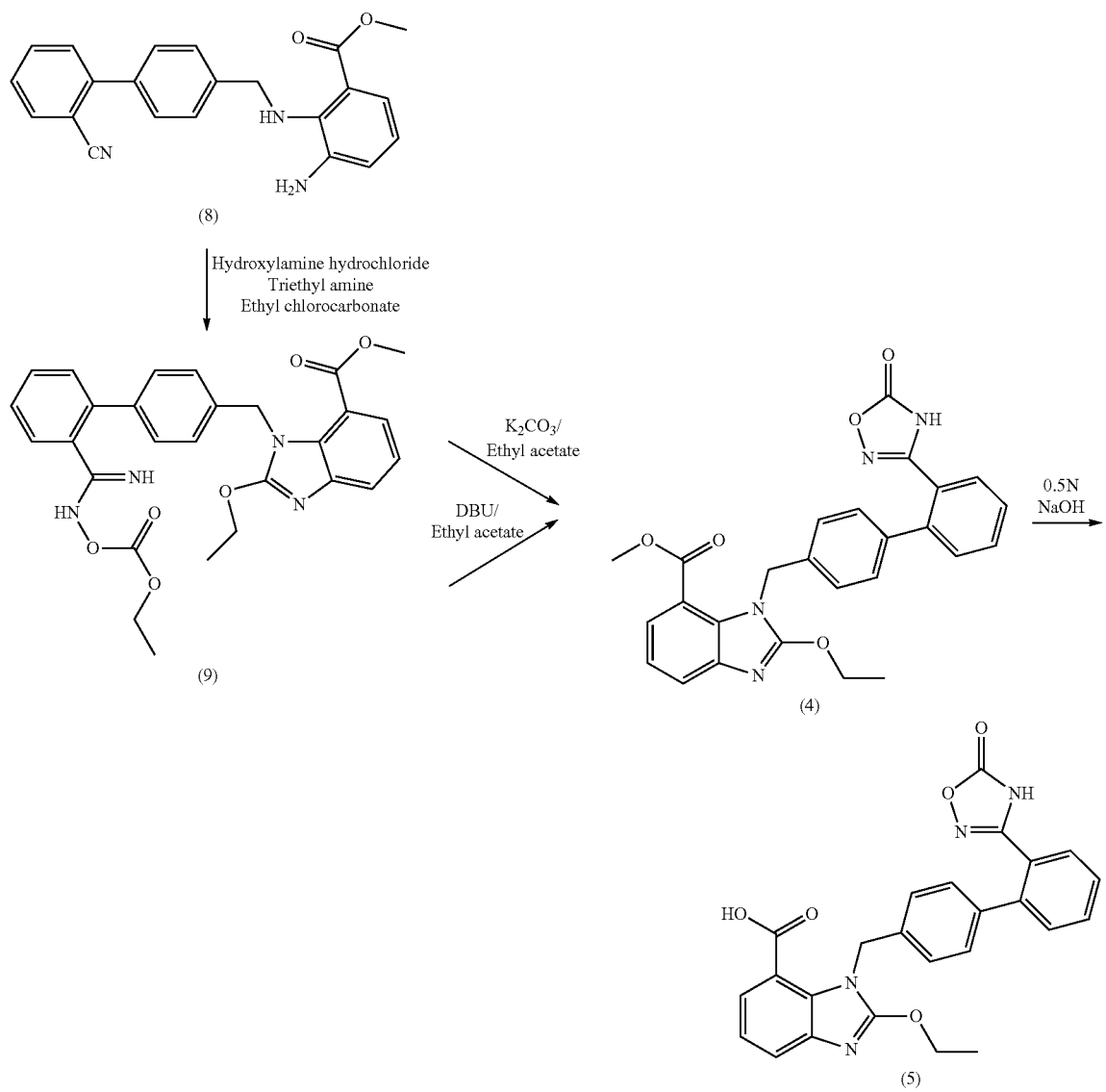

It is known that synthetic compounds can contain extraneous compounds or impurities resulting from their synthesis or degradation. The impurities can be unreacted starting materials, by-products of the reaction, products of side reactions, or degradation products. Generally, impurities in an active pharmaceutical ingredient (API) may arise from degradation of the API itself, or during the preparation of the API. Impu- J. Med. Chem. Vol. 39, No. 26, 5230-5237 (1996) follows the same reaction sequence with minor changes in reagents such as use of triethylamine as base during the conversion of cyano group to hydroxyamidino derivative of formula (3). When we repeat these processes for the preparation of hydroxyamidino derivative of formula (3), we obtain amide impurity of compound of formula (12) in approximately about 50% along with desired product, which accounts for the yield loss and impair the quality of the product. Such formation of impurity would demand the exhaustive purification.

Moreover, other processes as depicted in Schemes 2 and 3 disclosed in U.S. '054 involve multistep for the preparation of azilsartan and in turn azilsartan medoxomil. Also, these processes give low yield, thus making them to be economically expensive on commercial scale.

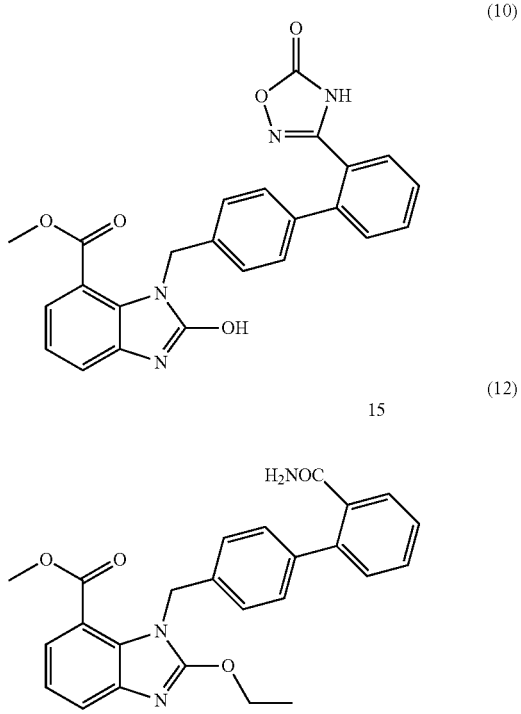

U.S. Pat. No. 7,157,584 discloses process for preparation of azilsartan medoxomil which process comprises reacting 1-[[2'-(4,5-dihydro-5-oxo-4H-1,2,4-oxadiazol-3-yl)biphenyl-4-yl]methyl]-2-ethoxy-1H-benzimidazole-7-carboxylic acid with 4-hydroxymethyl-5-methyl-1,3-dioxol-2-one in presence of dimethylacetamide, p-toluoyl sulfonylchloride, 4-dimethylaminopyridine and potassium carbonate.

Conversion of azilsartan (5) into azilsartan medoxomil (1) in high yield is important on higher scale, which demands improved process of preparation of medoxomil component such as 4-hydroxymethyl-5-methyl-1,3-dioxol-2-one (11), though there exist the literature such as *Synthetic communications*, 22(9), 1277-1282 (1992) for the preparation of 4-hydroxymethyl-5-methyl-1,3-dioxol-2-one (11).

Regulatory authorities worldwide require drug manufactures to isolate, identify and characterize the impurities in their products. Furthermore, it is required to control the levels of these impurities in the final drug substance obtained by the manufacturing process and to ensure that the impurity is present in the lowest possible levels and within the limits, even if structural determination is not possible.

Accordingly, there remains a need for highly pure azilsartan medoxomil substantially free of impurities, as well as purification processes for obtaining them on commercially economical scale.

DESCRIPTION OF THE INVENTION

The above-mentioned methods of preparation of azilsartan suffer from the drawbacks of multistep process, generating more impurities, compelling for purification steps, which decrease the yield of the reaction and impair the quality of the prepared azilsartan and in turn azilsartan medoxomil. It has also been found that azilsartan prepared according to the procedure described in the aforementioned process (Scheme 1) contains approximately about 50% amide impurity of formula (12) and 10-12% of the desethyl impurity of formula (10) and hence control is required in the drug compound manufacturing process to ensure that the impurity is present at the lowest possible levels.

The present invention has also been developed to improve the cyclization process of the hydroxyamidino compound of formula (3) to 1,2,4-oxadiazol derivative compound of formula (4). We also found that the major impurity formed during the cyclization step is desethyl impurity (10). To optimize the formation of 1,2,4-oxadiazol derivative compound of formula (4) and to reduce the formation of desethyl impurity, reaction was conducted under the influence of "carbonyl" source as referred in step (ii) below, and at low temperatures. By employing the above changes in the process, the improvements in the purity and yield were observed. Purity of the isolated 1,2,4-oxadiazol derivative compound of formula (4) is >95% having a reduced content of desethyl impurity i.e. less than approximately 0.2%.

Another embodiment of the invention involves azilsartan (5) having a reduced content of desethyl impurity (10) i.e. less than approximately 0.1%.

Further embodiment of the invention involves azilsartan medoxomil (1) having a reduced content of desethyl impurity (10) i.e. less than approximately 0.1%.

Therefore according to one of the embodiment the above-mentioned disadvantages can be overcome by the method of the invention, which involves method of preparing pure methyl 1-[[2'-(4,5-dihydro-5-oxo-4H-1,2,4-oxadiazol-3-yl)biphenyl-4-yl]methyl]-2-ethoxy-1H-benzimidazole-7-carboxylate an intermediate for azilsartan medoxomil with reduced content of desethyl impurity, without using column chromatography.

An another embodiment of the invention involves the novel and improved process for preparation of pure methyl 1-[[2'-(4,5-dihydro-5-oxo-4H-1,2,4-oxadiazol-3-yl)biphenyl-4-yl]methyl]-2-ethoxy-1H-benzimidazole-7-carboxylate an intermediate for azilsartan medoxomil with reduced content of desethyl impurity.

Yet another embodiment of the invention involves azilsartan medoxomil (1) having purity of more than 99%.

An another embodiment of the invention involves the conversion of methyl 2-ethoxy [[2'-(hydroxyamidino) biphenyl-4-yl]methyl]-1H-benzimidazole-7-carboxylate compound of formula (3) to methyl 1-[[2'-(4,5-dihydro-5-oxo-4H-1,2,4-oxadiazol-3-yl)biphenyl-4-yl]methyl]-2-ethoxy-1H-benzimidazole-7-carboxylate compound of formula (4) in a single step without involving multistep process as shown above in Scheme 2 and 3.

In an another embodiment the invention provides an improved process for the preparation of conversion of hydroxyamidino derivative of formula (3) from cyanobiphenyl derivative compound of formula (2) in presence of a base as mentioned below in step (i). Base used in step (i) can be selected from organic or inorganic bases. Inorganic base is selected from the group comprising of carbonate or bicarbonate of alkali or alkaline earth metals and the like. Use of above mentioned bases decreases the content of amide impurity (< about 5%) of compound of formula (12) in the said product with better yield (85-90%).

Further aspect of the invention involves an improved process for the preparation of hydroxyamidino derivative of formula (3) with reduced content i.e. less than about 5% of amide impurity of formula (12).

Yet further aspect of the invention involves an improved process for the preparation of hydroxyamidino derivative of formula (3) with purity more than 95%.

Yet another aspect of the invention involves an improved process for the preparation of azilsartan or azilsartan medoxomil with high yield, high degree of purity and less number of impurities.

In further aspect, the invention provides a process for the preparation of azilsartan or azilsartan medoxomil (Scheme 4) comprising:

reacting methyl 1-[(2'cyanobiphenyl-4-yl)methyl]-2-ethoxybenzimidazole-7-carboxylate of formula (2) with hydroxylamine or salt thereof in presence of a base to obtain methyl 2-ethoxy [[2'-(hydroxyamidino) biphenyl-4-yl]methyl]-1H-benzimidazole-7-carboxylate of formula (3);

(ii) reacting methyl 2-ethoxy [[2'-(hydroxyamidino) biphenyl-4-yl]methyl]-1H-benzimidazole-7-carboxylate of formula (3) with "carbonyl" source in presence of a suitable base to obtain methyl 1-[[2'-(4,5-dihydro-5-oxo-4H-1,2,4-oxadiazol-3-yl)biphenyl-4-yl]methyl]-2-ethoxy-1H-benzimidazole-7-carboxylate compound of formula (4);

(iii) hydrolysis of methyl 1-[[2'-(4,5-dihydro-5-oxo-4H-1,2,4-oxadiazol-3-yl)biphenyl-4-yl]methyl]-2-ethoxy-1H-benzimidazole-7-carboxylate compound of formula (4) to obtain 1-[[2'-(4,5-dihydro-5-oxo-4H-1,2,4-oxadiazol-3-yl)biphenyl-4-yl]methyl]-2-ethoxy-1H-benzimidazole-7-carboxylic acid (azilsartan);

(iv) optionally, reacting 1-[[2'-(4,5-dihydro-5-oxo-4H-1,2,4-oxadiazol-3-yl)biphenyl-4-yl]methyl]-2-ethoxy-1H-benzimidazole-7-carboxylic acid with 4-hydroxymethyl-5-methyl-1,3-dioxol-2-one to obtain (5-methyl-2-oxo-1,3-dioxol-4yl)methyl 2-ethoxy-1-[[2'-(4,5-dihydro-5-oxo-4H-1,2,4-oxadiazol-3-yl)biphenyl-4-yl]methyl]-2-ethoxy-1H-benzimidazole-7-carboxylate (azilsartan medoxomil);

(v) optionally, converting azilsartan medoxomil to its salt such as alkali or alkaline earth metal salt.

Base used in step (i) can be selected from organic or inorganic bases. Inorganic base is selected from the group comprising of carbonate, bicarbonate, hydroxides of alkali or alkaline earth metals and the like. The organic base is selected from the group comprising of pyridine, lutidine, diisopropylethylamine, dimethylaminopyridine, triethylamine and the like. The salt of hydroxyl amine in step (i) can be any salt such as hydrogen halide.

The "carbonyl" source as referred in step (ii) can be selected from compounds which can provide carbonyl moiety. The compound referred as "carbonyl" source can be selected from the group comprising of N,N-carbonyldiimidazole, dialkyl carbonate, phosgene equivalents, alkyl and aryl carbodimides such as N,N-diisopropylcarbodimide, N,N dicyclohexyl carbodimide, diphenyl carbodimide, ditolyl carbodiimide and the like.

Scheme 4

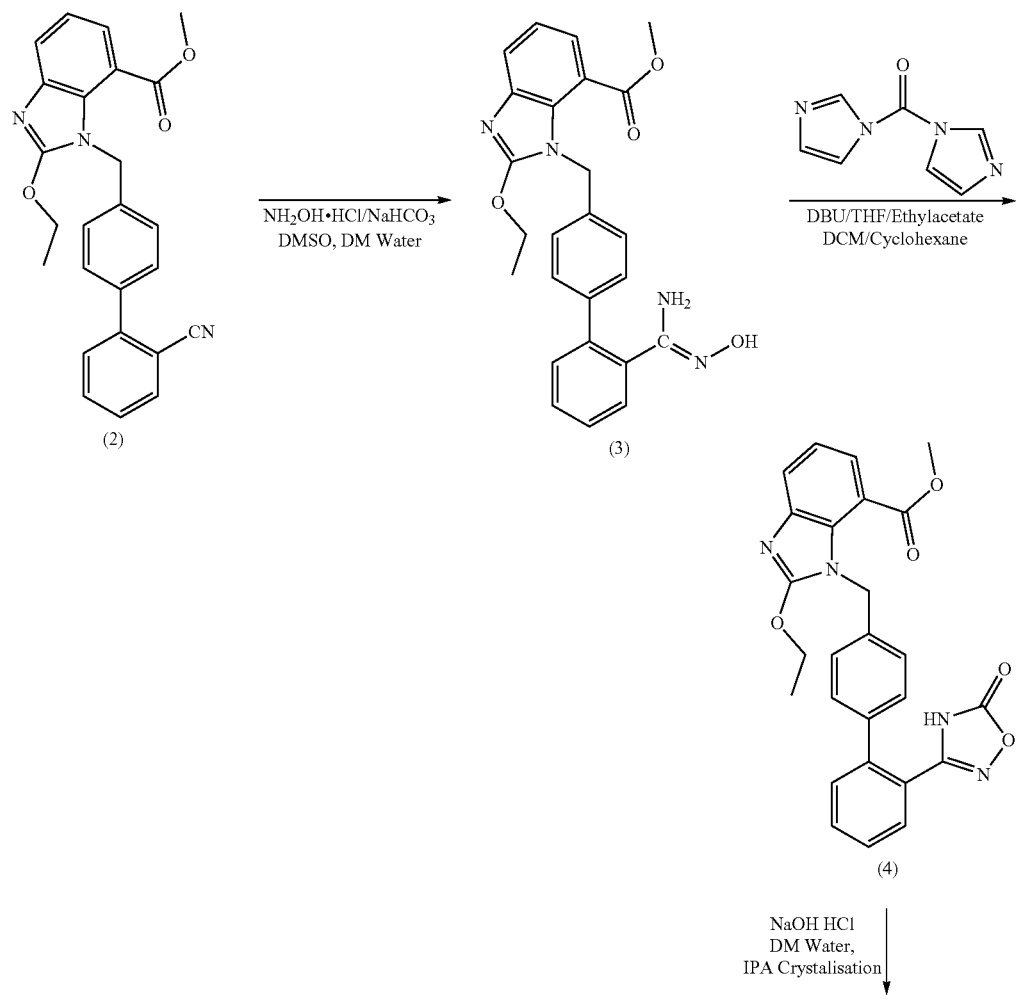

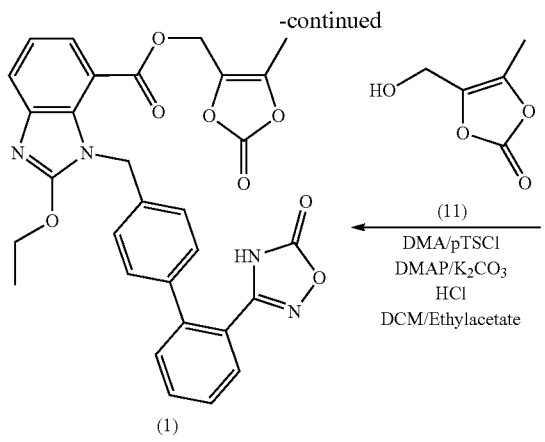
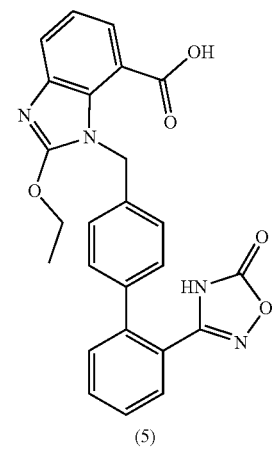

In yet another aspect, the invention provides a process for the preparation of azilsartan as mentioned in Scheme 4. The reaction shown in Scheme 4 can be carried out with or without isolation of any of the intermediates.

In an another aspect, the invention provides an improved process for the preparation of 4-hydroxymethyl-5-methyl-1,3-dioxol-2-one (11) with improved yield in comparison to prior art process disclosed in *Synthetic communications*, 22(9), 1277-1282 (1992) for the preparation of 4-hydroxymethyl-5-methyl-1,3-dioxol-2-one (11). The compound 4-hydroxymethyl-5-methyl-1,3-dioxol-2-one (11) is required for the ester formation i.e. for the preparation of azilsartan medoxomil from azilsartan. The invention disclosed in this article involves reaction of 4-chloromethyl-5-methyl-1,3-dioxol-2-one with formic acid in presence of triethylamine in acetonitrile to obtain ester derivative from which hydroxy compound (11) is obtained in 70-80% yield along with unknown impurity 10-20% after treating with 37% HCl/Methanol. According to process of the present invention hydroxy compound is prepared using IPA/HCl instead of 37% HCl/methanol, which gives improved purity of hydroxy compound up to 94-96%. When alkali metal iodide is used along with methanolic HCl the improved purity of hydroxy compound is obtained. Specifically, the hydrolysis in presence of methanolic HCl and sodium iodide gives purity of about 97%.

In yet another aspect of the invention, there is provided an improved process for the preparation of 4-hydroxymethyl-5-methyl-1,3-dioxol-2-one of formula (11). It involves reaction of 4-chloromethyl-5-methyl-1,3-dioxol-2-one with formic acid in presence of triethylamine in dichloromethane, which on further hydrolysis using methanolic HCl in presence of alkali metal iodide such as sodium iodide yields 4-hydroxymethyl-5-methyl-1,3-dioxol-2-one of formula (11) with purity of about 97%.

In yet another aspect of the invention, the azilsartan medoxomil has particles size having $d_{0.9}$ less than 200 micrometer, $d_{0.5}$ less than 50 micrometer and $d_{0.1}$ less than 10 micrometer.

In yet another aspect of the invention, the azilsartan medoxomil monopotassium salt has particles size having $d_{0.9}$ less than 50 micrometer, $d_{0.5}$ less than 30 micrometer and $d_{0.1}$ less than 15 micrometer.

In another aspect there is provided a pharmaceutical composition that includes a therapeutically effective amount of azilsartan medoxomil and salts thereof according to the process of the present invention and one or more pharmaceutically acceptable carriers, excipients or diluents.

In yet another aspect there is provided a use of a pharmaceutical composition that includes a therapeutically effective amount of azilsartan medoxomil and salts thereof according to the process of the present invention and one or more pharmaceutically acceptable carriers, excipients or diluents to treat conditions in a subject, in need thereof such as a strong and long lasting angiotensin II antagonistic activity and hypotensive action, and an insulin sensitizing activity, and which is useful as an agent for the prophylaxis or treatment of circulatory diseases such as hypertension, cardiac diseases (cardiac hypertrophy, cardiac failure, cardiac infarction and the like), nephritis, stroke and the like and metabolic diseases such as diabetes and the like.

The details of the process of the invention are provided in the Examples given below, which are provided by way of illustration only and therefore should not be construed to limit the scope of the invention.

EXAMPLES

Example 1

Preparation of methyl 2-ethoxy [[2'-(hydroxyamidino) biphenyl-4-yl]methyl]-1H-benzimidazole-7-carboxylate To a solution of hydroxylamine hydrochloride (122 g) and dimethylsulfoxide (1000 ml), Sodium bicarbonate (204 g) was added at 25-30° C., which was further heated to 45-50° C. To the resulting solution 1-[(2'cyanobiphenyl-4-yl)methyl]-2-ethoxy benzimidazole-7-carboxylate (40 g) was added and the resulting solution was heated to 85-90° C. followed by stirring at the same temperature for about 18 h. Reaction mass was cooled to 15-20° C. Water was added and the solution was stirred for 15-20 min at 15-20° C. The product was filtered, washed and dried to obtain title compound. (Yield: 38 g; 88%; (Purity: 87% with amide impurity 3.86%.

Example 2

Preparation of methyl 1-[[2'-(4,5-dihydro-5-oxo-4H-1,2,4-oxadiazol-3-yl)biphenyl-4-yl]methyl]-2-ethoxy-1H-benzimidazole-7-carboxylate To a solution of methyl 2-ethoxy [[2'-(hydroxyamidino) biphenyl-4-yl]methyl]-1H-benzimidazole-7-carboxylate (25 g) in tetrahydrofuran (700 ml), N,N-carbonyldiimidazole (15 g) and 1,8-diazabicyclo[5.4.0]undec-7-ene (DBU)(13 g) was added and resulting solution was stirred for 30-40 mins. at about 20-25° C. To the resulting solution ethyl acetate (700 ml) and saturated solution of sodium bisulphite (700 ml) was added. Organic layer was separated, washed with brine solution and evaporated under vacuum to concentrate the solution. Reaction mass was cooled to 20-25° C. and cyclohexane was added to it and the solution was stirred for about 20-25° C. Product was filtered and dichloromethane was charged to it followed by stirring. The product was filtered, washed and dried to obtain title compound. (Yield: 17.8 g; 68% (Purity: 96% with desethyl impurity 0.11%)

Example 3

Preparation of 1-[[2'-(4,5-dihydro-5-oxo-4H-1,2,4-oxadiazol-3-yl)biphenyl-4-yl]methyl]-2-ethoxy-1H-benzimidazole-7-carboxylic Acid (Azilsartan)

Methyl 1-[[2'-(4,5-dihydro-5-oxo-4H-1,2,4-oxadiazol-3-yl)biphenyl-4-yl]methyl]-2-ethoxy-1H-benzimidazole-7-carboxylate (30 g) and NaOH solution (0.4 N; 475 ml) was stirred at 50-55° C. for 30 min. Reaction mass was cool to 10-15° C. and water was added. The pH of the resulting solution was adjusted to 2-3 by using 2 N HCl. Reaction mass was stirred for 30 mins. at 20-25° C. The product was filtered and dried under vacuum. The resulting product was suspended in isopropyl alcohol and was stirred for 25-30 mins. at 40-45° C. The product was filtered, washed and dried to obtain title compound. (Yield: 22 g; 75%)

Example 4A

Preparation of 4-hydroxymethyl-5-methyl-1,3-dioxol-2-one

To a solution of 4-chloromethyl-5methyl-1,3-dioxol-2-one (50 g) in acetonitrile (500 ml), formic acid (45 g) was added at 20-25° C. and the reaction mass cool to 10-15° C. followed by addition of triethylamine (95 g). Reaction mass was heated to 60-65° C. and stirred at the same temperature for about 5-6 hrs. Reaction mass was cooled to 15-20° C., filtered and washed by acetonitrile. Filtrate was taken and acetonitrile was distilled out under vacuum to concentrate the solution. Reaction mass was cooled to 25-30° C. and ethyl acetate and water was added, followed by stirring for about 15-20 minutes at 25-30° C. Aqueous layer extracted with ethyl acetate and combined organic layer were washed with brine solution. Organic layer was separated and evaporated completely under vacuum below 35-40° C. To the oily mass, methanol was added and heated to reflux temperature. A solution of HCl in isopropyl alcohol was added and the resulting solution was refluxed for about 60-75 mins. Reaction mass was cooled to 30-35° C. Distilled out the solvent completely to obtain title compound as oily mass. (Yield: 34.6 g; 79%)

Example 4B

Preparation of 4-hydroxymethyl-5-methyl-1,3-dioxol-2-one

4-Chloromethyl-5-methyl-1,3-dioxol-2-one (25 g) was dissolved in dichloromethane (250 ml) at 20-25° C., sodium iodide (2.5 g) and formic acid (22 g) was added at 20-25° C. Resulting mixture was cooled to 10-15° C. and triethyl amine (46.8 g) was added at 10-15° C. in 20-25 minutes. Resulting mixture was stirred for 5.0-6.0 hrs at 40-45° C., cooled to 20-25° C. and added DM water (250 ml). Organic layer was separated and washed with brine solution, and distilled out. Residue was dissolved in methanol (300 ml), methanolic HCl was added drop wise and resulting mixture was stirred for 1 hrs at 60-65° C. Active charcoal (1 g) was added to the reaction mass and stirred for 20-25 minutes at 50-55° C. Reaction mass was filtered through hyflo bed and bed was washed by MeOH (12 ml). The filtrate was evaporated under vacuum at 40-45° C. Obtained product was diluted with ethyl acetate (75 ml) and evaporated under vacuum to remove methanol content. (Yield: 0.67 g; 76.5%)

Example 5

Preparation of (5-methyl-2-oxo-1,3-dioxol-4yl)methyl 2-ethoxy-1-[[2'-(4,5-dihydro-5-oxo-4H-1,2,4-oxadiazol-3-yl)biphenyl-4-yl]methyl]-2-ethoxy-1H-benzimidazole-7-carboxylate (Azilsartan Medoxomil)

To a solution of 1-[[2'-(4,5-dihydro-5-oxo-4H-1,2,4-oxadiazol-3-yl)biphenyl-4-yl]methyl]-2-ethoxy-1H-benzimidazole-7-carboxylic acid (5 g) in dimethylacetamide (55 ml), 4-hydroxymethyl-5-methyl-1,3-dioxol-2-one (2 g) was added at about 20-25° C. followed by cooling of the resulting solution to about −10 to −15° C. To the resulting solution p-toluoyl sulfonylchloride (3 g), 4-dimethylaminopyridine (0.3 g) and $K_2CO_3$ (2 g) was added at −10 to −15° C. Temperature was slowly raised to 10-15° C. in about 1-2 hrs followed by stirring at the same temperature for about 5-6 hrs. Water was added to the resulting solution at 15-20° C. The pH of the solution was adjusted to 4-5 by using 0.5N HCl solution followed by stirring for about 30 mins. The product was filtered, washed and dried to obtain title compound. (Yield: 5 g; 81%)

Example 6

Purification of (5-methyl-2-oxo-1,3-dioxol-4yl)methyl 2-ethoxy-1-[[2'-(4,5-dihydro-5-oxo-4H-1,2,4-oxadiazol-3-yl)biphenyl-4-yl]methyl]-2-ethoxy-1H-benzimidazole-7-carboxylate (Azilsartan Medoxomil)

The crude azilsartan medoxomil was suspended in dichloromethane (15 ml) and ethyl acetate (15 ml) at 20-25° C. followed by stirring for 25-30 mins. at 40-45° C. The product thus obtained was filtered at 15-20° C. The resulting product was further suspended in dichloromethane (15 ml) and ethyl acetate (15 ml) solution at 20-25° C. followed by stirring for 25-30 mins at 40-45° C. The product was filtered, washed and dried to obtain title compound. (Yield: 3.6 g; 72%)

Example 7

Purification of (5-methyl-2-oxo-1,3-dioxol-4yl)methyl 2-ethoxy-1-[[2'-(4,5-dihydro-5-oxo-4H-1,2,4-oxadiazol-3-yl)biphenyl-4-yl]methyl]-2-ethoxy-1H-benzimidazole-7-carboxylate (Azilsartan Medoxomil)

The crude azilsartan medoxomil (20 g) was suspended in dichloromethane (40 ml) and ethyl acetate (40 ml) at 20-25° C. followed by stirring for 10-15 mins. at 40-45° C. and then cooled to 10°-15° C. and stirred for 15 minutes at same temperature. The product thus obtained was filtered and further suspended in a mixture of dichloromethane (15 ml) and ethyl acetate (15 ml) at 40-45° C. and then cooled to 10°-15° C. and stirred for 15 mins. at same temperature. The product was filtered, washed and dried to obtain title compound. The particle size obtained is $d_{0.1}$=1.8 μm, $d_{0.5}$=6.1 μm and d0.9=14.4 μm.

Example 8

Preparation of Azilsartan Medoxomil Monopotassium Salt

Azilsartan Medoxomil (1 g) was dissolved in acetone (25 ml) at 40-45° C. and the resulting solution was passed through hyflo to get cleared solution. The mixture was cooled to 20-25° C. and the solution of potassium 2-ethylhexanoate (1.6 g) in acetone (4 ml) was added drop wise in 10-15 min. The mixture was stirred for two hours at 20-25° C. The precipitated crystals were collected by filtration. (Yield: 0.65 g)

The invention claimed is:

1. A process for the preparation of azilsartan or its esters or salts thereof comprising reacting methyl 2-ethoxy[(2'-(hydroxyamidino)biphenyl-4-yl]methyl]-1H-benzimidazole-7-carboxylate of formula (3) with "carbonyl" source in presence of a suitable base to obtain methyl 1-[[2'-4,5-dihydro-5-oxo-:-4H-1,2,4-oxadiazol-3-yl) biphenyl-4-yl]methyl]-2-ethoxy-1H-benzimidazole-7-carboxylate of formula (4);

(3)

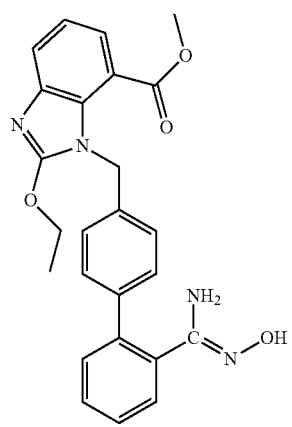

(4)

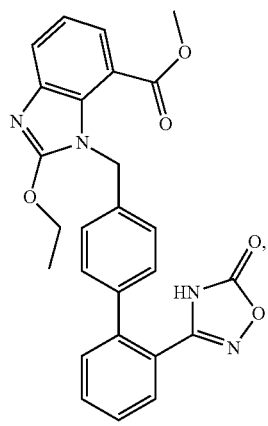

wherein "carbonyl" source can be selected from the group consisting of N,N carbonyldiimidazole, dialkyl carbonate, phosgene equivalents viz phosgene, diphosgene and triphosgene, alkyl and aryl carbodiimides selected from the group comprising of N,N-diisopropylcarbodiimide, N,N-dicyclohexyl carbodiimide, ditolyl carbodiimide; and preparing azilsarstan or its esters or salts thereof.

2. The process according to claim 1, comprising reacting methyl 1-[(2'cyanobiphenyl-4-yl)methyl]-2-ethoxybenzimidazole-7-carboxylate of formula (2)

(2)

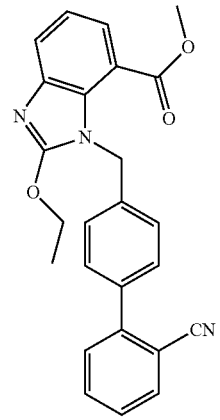

with hydroxylamine or salt thereof in presence of a base to obtain methyl 2-ethoxy[(2'-(hydroxyamidino)biphenyl-4-yl]methyl]-1H-benzimidazole-7-carboxylate of formula (3);

(3)

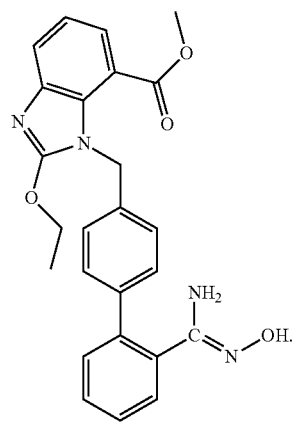

3. The process according to claim 1, further comprising the steps of:
(i) hydrolysis of methyl 1-[[2'-4,5-dihydro-5-oxo-4H-1,2,4-oxadiazol-3-yl) biphenyl-4-yl]methyl]-2-ethoxy-1H-benzimidazole-7-carboxylate of formula (4) to obtain 1-[[2'-4,5-dihydro-5-oxo-4H-1,2,4-oxadiazol-3-yl)biphenyl-4-yl]methyl]-2-ethoxy-1H-benzimidaz-ole-7-carboxylic acid (azilsartan) of formula (5);

(5)

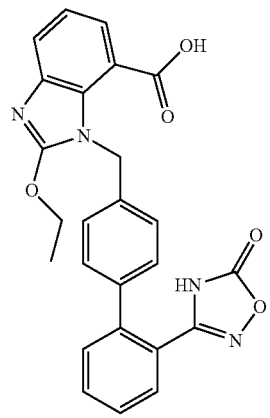

(ii) optionally, reacting 1-[[2'-4,5-dihydro-5-oxo-4H-1,2,4-oxadiazol-3-yl) biphenyl-4-yl]methyl]-2-ethoxy-1H- benzimidazole-7-carboxylic acid of formula (5) with 4-hydroxymethyl-5-methyl-1,3-dioxol-2-one of formula (11);

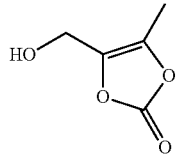
(11)

to obtain (5-methyl-2-oxo-1,3-dioxol-4yl)methyl 2-ethoxy-1-[[2'-(4,5-dihydro-5-oxo-4H-1,2,4-oxadiazol-3-yl) biphenyl-4-yl]methyl]-2-ethoxy-1H-benzimidazole-7-carboxylate (azilsartan medoxomil) of formula (1); and

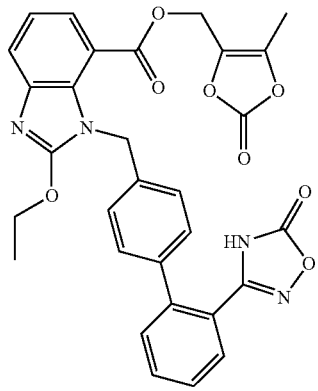
(1)

(iii) optionally, converting azilsartan medoxomil to its salt selected from alkali or alkaline earth metal salt.

4. The process according to claim 2, wherein base used is selected from organic or inorganic bases.

5. The process according to claim 4, wherein inorganic base is selected from the group comprising of carbonate, bicarbonate and hydroxide of alkali or alkaline earth metal.

6. The process according to claim 4, wherein organic base is selected from the group comprising of pyridine, lutidine, diisopropylethylamine, dimethylaminopyridine and triethylamine.

7. The process according to claim 5, wherein inorganic base sodium bicarbonate.

8. The process according to claim 2, wherein salt of hydroxyl amine is hydrogen halide.

9. The process according to claim 1, having particle size distribution of azilsartan medoxomil wherein, $d_{0.1}$ less than 15 μm, $d_{0.5}$ less than 30 μm and $d_{0.9}$ less than 50 μm.

10. The process according to claim 9, having particle size distribution of azilsartan medoxomil wherein, $d_{0.1}$ less than 5 μm, $d_{0.5}$ less than 10 μm and $d_{0.9}$ less than 25 μm.

11. The process according to claim 1, having particle size distribution of azilsartan medoxomil monopotassium salt wherein, $d_{0.1}$ less than 50 μm, $d_{0.5}$ less than 100 μm and $d_{0.9}$ less than 200 μm.

12. The process according to claim 11, having particle size distribution of azilsartan medoxomil monopotassium salt wherein, $d_{0.1}$ less than 25 μm, $d_{0.5}$ less than 70 μm and $d_{0.9}$ less than 150 μm.

* * * * *